US006306661B1

(12) United States Patent
Lakowicz et al.

(10) Patent No.: US 6,306,661 B1
(45) Date of Patent: Oct. 23, 2001

(54) WATER SOLUBLE LUMINESCENCE OXYGEN SENSOR AND METHOD

(75) Inventors: Joseph R. Lakowicz, 10037 Fox Den Rd., Ellicott City, MD (US) 21042; Felix Castellano, Columbia, MD (US)

(73) Assignee: Joseph R. Lakowicz, Ellicott City, MD (US)

( * ) Notice: Subject to any disclaimer, the term of this patent is extended or adjusted under 35 U.S.C. 154(b) by 0 days.

(21) Appl. No.: 09/019,120

(22) Filed: Feb. 5, 1998

(51) Int. Cl.[7] .................................................. G01N 33/00
(52) U.S. Cl. ........................ 436/138; 436/127; 436/136; 436/172
(58) Field of Search .................................... 436/127, 136, 436/138, 172; 546/27, 49, 81, 88, 255, 257, 262, 264, 300–301; 422/56

(56) References Cited

U.S. PATENT DOCUMENTS

| | | | |
|---|---|---|---|
| 4,745,076 | * 5/1988 | Müller et al. | 436/537 |
| 5,030,420 | * 7/1991 | Bacon et al. | 422/82.07 |
| 5,242,835 | * 9/1993 | Jensen | 436/136 |
| 5,585,279 | * 12/1996 | Davidson | 436/546 |

FOREIGN PATENT DOCUMENTS

340605 * 11/1989 (EP).

OTHER PUBLICATIONS

F. A. Cotton Advanced Inorganic Chemistry 1980, John Wiley & Sons, Inc.: New York, pp. 74–77.*
J. M. Vanderkooi et al, J. Biol. Chem. Apr. 1987, 262, 5476–5482.*
J. M. Vanderkooi et al. Biochemistry Jun. 1990, 29, 5332–5338.*
J. W. Park et al, J, Photochem. Photobiol. Feb. 1995, 86, 89–95.*
J.N. Demas et al. Anal. Chem. 1976, 48, 353–357.*
J.N. Demas et al. J. Am. Chem. Soc. 1977, 99, 3547–3551.*
P.J. Giordano et al. J. Am. Chem. Soc. 1978, 100, 6960–6965.*
W.R. Midden et al. J. Inorgan. Biochem. 1980, 12, 93–105.*
S.L. Shapiro et al. Springer Ser. Chem. Phys. 1980, 14, 227–231.*
J.L. Cline III et al. J. Phys. Chem. 1985, 89, 94–97.*
O.S. Wolfbeis et al. Mikrochim. Acta. 1986, 3, 359–366.*
L.A. Basile et al. J. Am. Chem. Soc. 1987, 109, 7548–7550.*
W. Bannwarth et al. Helv. Chim. Acta 1988, 71, 2085–2099.*
P. Boublikova et al. Gen. Physiol. Biophys. 1989, 8, 475–490.*
T. Iyoda et al. J. Chem. Soc., Faraday Trans. 1991, 87, 1765–1769.*
P.V. Kamat et al. Photochem. Photobiol. 1992, 55, 159–163.*
P.L. Cannon Jr. et al. in "Electrochemistry in Colloid and Dispersions" 1992, VCH Publishers, Inc.: New York, pp. 147–161.*
S.M. Zakeeruddin et al. J. Electroanal. Chem. 1992, 337, 253–283.*
K. Kalyanasundaram et al. Chem. Phys. Lett. 1992, 193, 292–297.*
L. Sacksteder et al. Anal. Chem. 1993, 65, 3480–3483.*
M.K. Nazeeruddin et al. J. Phys. Chem. 1993, 97, 9607–9612.*
I. Klimant et al. Talanta 1994, 41, 985–991.*
Q.G. Mulazzani et al. J. Phys. Chem. 1994, 98, 1145–1150.*
C. Richardson et al. J. Chem. Soc., Chem. Commun. 1995, 1821–1823.*
H. Huesmann et al. Thin Solid Films 1996, 284–285, 62–65.*
B. Ullrich et al. Proc. SPIE–Int. Soc. Opt. Eng. 1986, 2699, 88–95.*
R.–J. Lin et al. Inorg. Chim. Acta 1996, 242, 179–183.*
D. Yoo et al. Mater. Res. Soc. Symp. Proc. 1996, 413, 395–400.*
D. Garcia–Fresnadillo et al. Helv. Chim. Acta 1996, 79, 1222–1238.*
J.–K. Lee et al. Appl. Phys. Lett. 1996, 69, 1686–1688.*
X.–Q. Guo et al. Anal. Biochem. 1997, 254, 179–186.*
F.N. Castellano et al. Photochem. Photobiol. 1998, 67, 179–183.*
H. Szmacinski et al. Biochim. Biophys. Acta. 1998, 1383, 151–159.*
Shabbir Bambot et al., "Phase Fluorometric Sterilizable Optical Oxygen Sensor," Biotechnology and Bioengineering, vol. 43, pp. 1139–1145, 1994.
M.E. Cox et al., "Detection of oxygen by fluorescence quenching", Applied Optics, vol. 24, No. 14, pp. 2114–2120, Jul. 15, 1985.
M.E. Cox et al., "The Use of Fluorescence Quenching To Measure Oxygen Concentration," SPIE, vol. 576, Optical Fibers in Medicine and Biology (1985), pp. 60–65.
Eric D. Lee et al. "Luminescence Ratio Indicators for Oxygen," Anal. Chem., vol. 59, pp. 279–283, 1987.
Joseph R. Lakowicz et al., "Frequency–Domain Fluorescence Spectroscopy", Topics in Fluroescence Spectroscopy, vol. 1: Techniques, pp. 293–354, 1991.
Susan Anderson et al., "Preparation and Characterisation of 2,2'–Bipyridine–4,4'–disulphonic . . . Acid", J. Chem. Soc., Dalton Trans., pp. 2247–2261, 1985.

(List continued on next page.)

*Primary Examiner*—Arlen Soderquist
(74) *Attorney, Agent, or Firm*—Rothwell, Figg, Ernst & Manbeck

(57) ABSTRACT

The oxygen concentration of a sample is determined utilizing a water-soluble metal ligand complex which is brought into interactive proximity with the sample to form a mixture. The mixture is irradiated with electromagnetic light energy so as to cause emission of light indicative of oxygen. The emitted light is measured, and the measurement utilized so as to determine oxygen concentration of the sample.

9 Claims, 15 Drawing Sheets

OTHER PUBLICATIONS

J.R. Bacon et al., "Determination of Oxygen Concentrations by Luminescence Quenching . . . Complex," Anal. Chem., vol. 59, pp. 2780–2785, 1987.

Dmitri Papkovsky, "Phosphorescent Complexes of Porphyrin Ketones: Optical Properties and Application to Oxygen Sensing," Anal. Chem., vol. 67, pp. 4112–4117, 1995.

W.M. Vaughan et al., "Oxygen Quenching of Pyrenebutyric Acid Fluorescence in Water. A Dynamic Probe of the Microenvironment," Biochemistry, pp. 464–473.

* cited by examiner

[Ru(dpp(SO₃Na)₂)₂(dcbee)]Cl₂

[Ru(dpp(SO₃Na)₂)₂(dcbmgly)]Cl₂

[Os(dpp(SO₃Na)₂)₃]Cl₂

[Re(dpp(SO₃Na)₂)(CO)₃(Py-COOEt)](PF₆)

[Re(bcp)(CO)₃(Py-SO₃Na)](PF₆)

$[Os(dpp(SO_3Na)_2)_3]^{2+}$ $[Re(dpp(SO_3Na)_2)(CO)_3(Py-COOEt)]^+$ $[Re(bcp)(CO)_3(Py-SO_3Na)]^+$ Ru(dpp(SO₃Na)₂(phen-IA)(CN)₂

[Ru(dpb(SO₃Na)₂)(bpy)(phen-mal)]²⁺

[Re(dpp(SO₂Cl)₂)(CO)₃(Py-SO₃H)]⁺

[Os(phen-NCS)(CN)₄]²⁻

WATER SOLUBLE LUMINESCENCE OXYGEN SENSOR AND METHOD

STATEMENT REGARDING FEDERALLY SPONSORED RESEARCH

This invention was made with government support in the form of grants nos. RR-08119 and 1-F32-GM18653 from the United States Department of Health and Human Services, National Institutes of Health. The government may have certain rights in the invention.

BACKGROUND OF THE INVENTION

1. Technical Field

This invention relates to the measurement of dissolved oxygen concentrations in solution.

2. Description of the Background Art

Fluorescent probes for oxygen sensing are of great interest because of their high sensitivity and potential specificity. Importantly, metal ligand complexes display luminescent decay times from 100 ns to 100 $\mu$s. As a consequence, metal ligand complex probes extend the observable time scale of decay measurements by orders of magnitude over other routinely used fluorophores. A variety of fluorophores with longer lifetimes have been used as indicators of dissolved oxygen (Vaughan, W. M. et al., *Biochemistry* 9:464–473 (1970); Cox, M. E. et al., *App. Optics* 24(14):2114–2120 (1985)).

Quenching of fluorescence by oxygen is one of the earliest observations in fluorescence quenching. Long lifetime phosphorescent porphyrins also have been developed for this use (Papkovsky, D. B. et al., *Anal. Chem.*, 67:4112–4117 (1995)). One of the most widely used oxygen sensors has been ruthenium-(4,7-diphenyl-1,10-phenanthroline)$_3$ ([Ru(dpp)$_3$]$^{2+}$). The favorable optical properties of this complex have resulted in considerable effort to improve the performance of oxygen sensors based on this luminescent metal-ligand complex. Additionally, sensors based on [Ru(dpp)$_3$]$^{2+}$ are highly stable and can be steam sterilized (Bambot, S. B. et al. *Biotech. Bioengr.*, 43:1139–1145 (1994)), facilitating use for medical purposes.

To further improve the spectral properties of these long lifetime oxygen sensors, metal-ligand complexes excitable with green light have been developed, as have oxygen sensors which can be excited above 600 nm. These long wavelength oxygen sensors allow measurements through skin (Bambot, S. B. et al., *Biosensors & Bioelectronics* 10:643–652 (1995)), allowing minimally invasive transdermal sensing of oxygen concentration in body tissues.

The measurement of decay times of the oxygen sensor instead of its fluorescence intensity is preferred in this minimally invasive oxygen sensing in the body because decay times can be easily measured in turbid media and through skin (Szmacinski, H. et al., *Sensors and Actuators B* 30:207–215 (1996)).

However, all the previously known fluorophores were insoluble in water and were either dissolved in organic solvents, or were contained in polymeric or silicon supports (Bacon, J. R. et al., *Anal. Chem.*, 59:2780–2785 (1987)). These fluorophores thus were not desirable for use in the body of a living animal or for samples incompatible with organic solvents.

In the past, tissue hypoxia was diagnosed in critically ill patients by an indirect method which was time-intensive and required simultaneous measurements of arterial and venous hemoglobin saturation and measurements of cardiac output and lactate concentration. This prior art method was difficult to perform, and revealed little about the oxygen concentration in tissues or in any particular tissues of interest. Therefore, there is a need for improved methods and oxygen sensors, and which can allow immediate determination of oxygen concentrations in the tissues of the body without the need for techniques such as phlebotomy.

SUMMARY OF THE INVENTION

In accordance with the present invention, a method of conducting an assay of a sample containing oxygen, comprises forming a mixture so as to bring a water-soluble metal-ligand complex into interactive proximity with a sample containing oxygen. The mixture is irradiated with electromagnetic light energy so as to cause emission of light indicative of oxygen in the sample, and the emitted light is measured. The measurement of the emitted light is utilized so as to measure oxygen concentration of the sample.

DETAILED DESCRIPTION OF THE PREFERRED EMBODIMENTS

Figure 1:
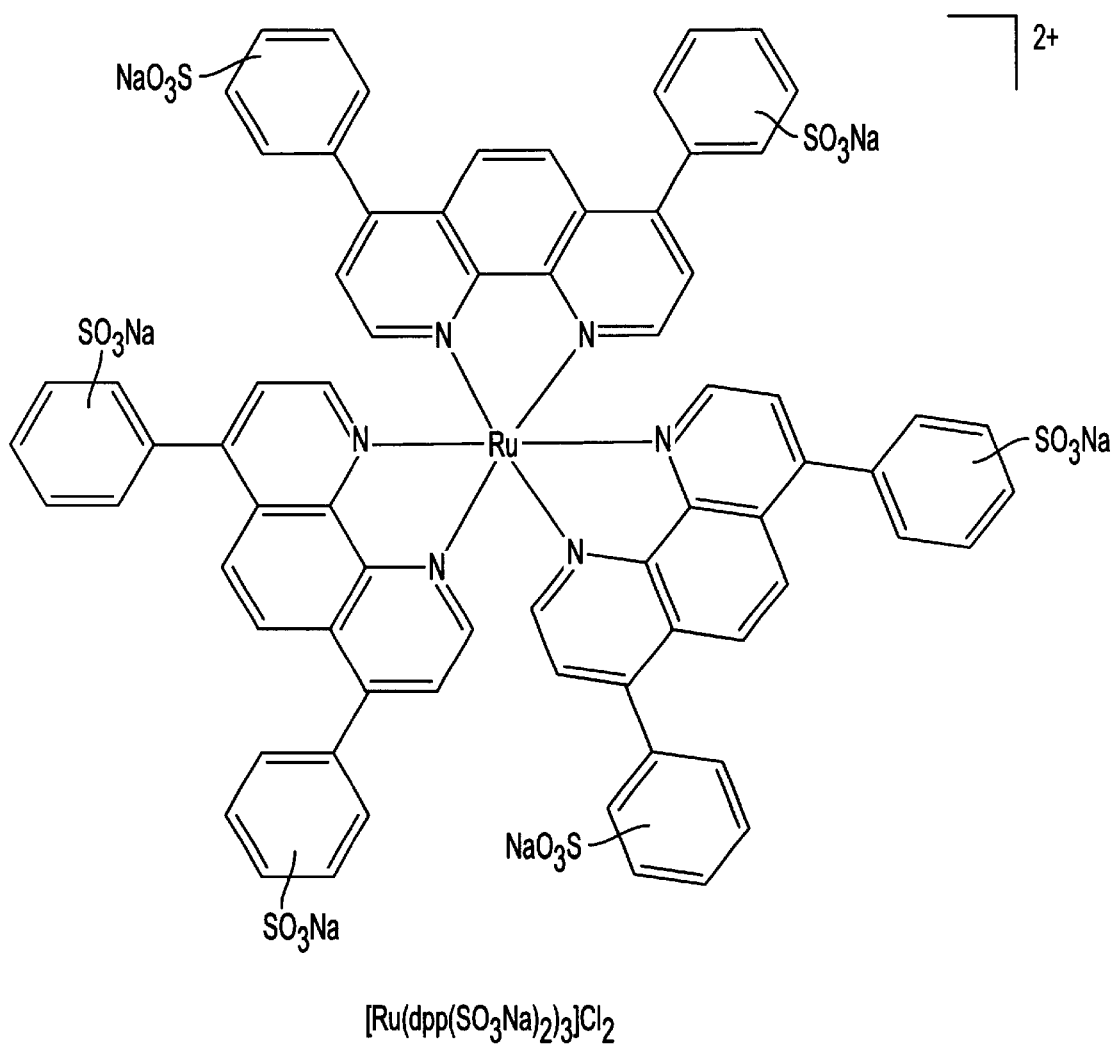
FIG. 1 shows the chemical structure of the preferred inventive water soluble oxygen sensor.

According to one aspect, the present invention is directed to a method of conducting an assay of a sample containing oxygen, as outlined above. The invention utilizes water-soluble metal-ligand complexes which are mixed with an oxygen-containing sample. Preferred water-soluble metal-ligand complexes in accordance with the present invention have a water solubility within the range of about 0.1 mg/ml to about 500 mg/ml, preferably greater than about 1 mg/ml, and most preferably about 10 mg/ml or greater.

The present invention utilizes transition metals in the water-soluble metal ligand complexes. In preferred embodiments, the transition metals used are Ruthenium (Ru), Rhenium (Re) and Osmium (Os).

The meanings of other symbols or abbreviations used herein include:

| SYMBOL OR ABBREVIATION | CHEMICAL NAME |
| --- | --- |
| bpy | 2,2'-bipyridine |
| phen | 1,10-phenanthroline |
| phen-NCS | 5-isothiocyanate-1,10-phenanthroline |
| phen-IA | 5-iodoacetamido-1,10-phenanthroline |
| bpy(NHS)$_2$ | 4,4'-N-hydroxysuccidimidyl ester-2,2'-bipyridine |
| dpb | 4,4'-diphenyl-2,2'-bipyridine |
| dpp | 4,7-diphenyl-1,10-phenanthroline |
| dpp(SO$_3$Na)$_2$ | 4,7-bathophenanthroline-disulfonic acid, disodium salt |
| dcbee | 4,4'-diethyl ester-2,2'-bipyridine |
| dcbmgly | 4,4'-methyl glycolate ester-2,2'-bipyridine |
| CO | carbon monoxide |
| Py-COOEt | 4-ethyoxycarbonylpyridine |
| bcp | bathocuproine phenanthroline |
| CN | cyanide or cyano- |
| bpy(NCS)$_2$ | 4,4'-isothiocyanate-2,2'-bipyridine |
| phen-mal | 5-maleimide-1,10-phenanthroline |
| dpp(SO$_2$Cl)$_2$ | 4,7-bathophenanthroline-disulfonyl chloride |
| Py-SO$_3$H | 3-pyridine sulfonic acid |

According to one embodiment, the invention is applicable to a composition comprising a chemical moiety having the formula

[M(P)$_m$(L$^1$)$_n$(L$^2$)$_o$(L$^3$)$_p$(L$^4$)$_q$(L$^5$)$_r$(L$^6$)$_s$]$_t$(B)$_u$ wherein M is ruthenium, osmium, or rhenium P is a polydentate ligand of M L$^1$, L$^2$, L$^3$, L$^4$, L$^5$, and L$^6$ are ligands of M, each of which may be the same or not the same as the other ligands, each of which may be a substance covalently bound to one or more of P, L$^1$, L$^2$, L$^3$, L$^4$, L$^5$, or L$^6$ through one or more amide, amine, or carbon linkages. Additionally, at least one of L$^1$, L$^2$, L$^3$, L$^4$, L$^5$, or L$^6$ may be a polydentate heterocyclic ligand, at least one of which may contain nitrogen. If the moiety has greater than one polydentate ligand, the polydentate ligands may be the same or different. At least one of P, L$^1$, L$^2$, L$^3$, L$^4$, L$^5$, or L$^6$ contain at least one substituent group that allows for significant water solubility. Preferred groups for water solubility include but are not limited to SO$_3$H, SO$_3$Na, SO$_3$K, NMe$_3$, NBu$_3$, and the like.

In addition, P, L$^1$, L$^2$, L$^3$, L$^4$, L$^5$, or L$^6$ may or may not contain groups available for the direct modification of biological macromolecules. The preferred groups for labeling biological macromolecules are N-hydroxysuccinimide esters, sulfonyl chlorides, isothiocyanates, iodoacetamides, and maleimides.

m is an integer of from 1 to about 10.

each of n, o, p, q, r, and s is zero or an integer of from 1 to about 10.

t is zero or an integer of from 1 to about 10.

u is zero or an integer of from 1 to about 10.

B is a biological substance, a synthetic substance which is capable of binding a biological substance, or a non-biological polymer.

P, L$^1$, L$^2$, L$^3$, L$^4$, L$^5$, or L$^6$, and B being such composition and number that the chemical moiety can be induced to photoluminescence when exposed to electromagnetic or electrical radiation, and the total number of bonds to M provided by the ligands to be equal to the coordination number of M.

Examples of polydentate ligands containing nitrogen that can be P and/or L$^1$–L$^6$ include bipyridyl, substituted bipyridyl, phenanthrolyl, substituted phenanthrolyl, bipyrazyl, substituted bipyrazyl, which may or may not be substituted by an alkyl, aryl, arylalkyl, carboxylate, carboxaldehyde, carboxamide, cyano, amino, hydroxycarbonyl, hydroxamido, aminocarbonyl, amidine, guanidinium, ureide, sulfonyl chloride, isothiocyanate, and other sulfur containing groups, phosphorous-containing group, maleimide, iodoacetamide, or the carboxylate ester of N-hydroxysuccinimide, and the like.

Examples of monodentate ligands that can be L$^1$–L$^6$ include carbon monoxide, cyanides, isocyanides, halides, aliphatic and aromatic substituted phosphines, amines, stilbines, arsines, and the like.

Examples of polydentate ligands without nitrogen include aliphatic and aromatic substituted heterocyclic phosphines, amines, stilbines, arsines, and the like.

Examples of B, which are biological/nonbiological macromolecules to be labelled include whole cell, subcellular particle, polypeptide, enzyme, protein, nucleic acid, DNA, RNA, polysaccharide, alkaloid, steroid, vitamin, amino acid, membrane, lipid, or any amine or sulfhydryl containing soluble or nonsoluble non-biological polymer, and the like.

The present invention also is directed toward water soluble metal ligand complexes which function as oxygen sensors. In one aspect, the invention provides a water soluble metal ligand complex selected from the group consisting of ([Ru(dpp(SO$_3$Na)$_2$)$_2$(dcbee)]Cl$_2$), ([Ru(dpp (SO$_3$Na)$_2$)$_2$(dcbmgly)]Cl$_2$), ([Os(dpp(SO$_3$Na)$_2$)$_3$]Cl$_2$), ([Re(dpp (SO$_3$Na)$_2$)) (CO)$_3$(Py-COOEt)](PF$_6$)), ([Re(bcp)(CO)$_3$ (Py-SO$_3$Na)](PF$_6$)), and ([Ru(4,7-diphenyl-1,10-phenanthroline(SO$_3$Na)$_2$)$_3$]Cl$_2$ 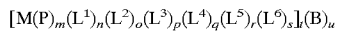 (Ru(dpp(SO$_3$Na)$_2$)$_3$]Cl$_2$)). The invention provides a preferred water soluble metal ligand complex of the formula [Ru(4,7-diphenyl-1,10-phenanthroline (SO$_3$Na)$_2$)$_3$]Cl$_2$. These structures have long decay times of the non-water soluble forms of these compounds. The long decay times indicate sensitivity to oxygen. Therefore, the inventive metal ligand complexes are useful as oxygen sensors.

Accordingly, in another aspect, the present invention provides a method for determining dissolved oxygen concentrations in a liquid using water soluble oxygen sensors selected from the group consisting of [Ru(dpp(SO$_3$Na)$_2$)$_2$ (dcbee)]Cl$_2$, [Ru(dpp(SO$_3$Na)$_2$)$_2$(dcbmgly)]Cl$_2$, [Os(dpp (SO$_3$Na)$_2$)$_3$]Cl$_2$, [Re(dpp(SO$_3$Na)$_2$))(CO)$_3$(Py-COOEt)] (PF$_6$), [Re(bcp)(CO)$_3$(Py-SO$_3$Na)](PF$_6$), and [Ru(4,7-diphenyl-1,10-phenanthroline(SO$_3$Na)$_2$)$_3$]Cl$_2$. In a further aspect, the invention provides for kits for determining the dissolved oxygen level in a solution using water soluble oxygen sensors selected from the group comprising [Ru(dpp(SO$_3$Na)$_2$)$_2$(dcbee)]Cl$_2$, [Ru(dpp(SO$_3$Na)$_2$)$_2$(dcbmgly)]Cl$_2$, [Os(dpp(SO$_3$Na)$_2$)$_3$]Cl$_2$, [Re(dpp(SO$_3$Na)$_2$))(CO)$_3$(Py-COOEt)](PF$_6$), [Re(bcp)(CO)$_3$(Py-SO$_3$Na)](PF$_6$), and [Ru(4,7-diphenyl-1,10-phenanthroline(SO$_3$Na)$_2$)$_3$]Cl$_2$. It is believed that these are the first practical water-soluble oxygen sensors. The absorption maximum near 480 nm, long lifetime, and large Stokes' shift, allows these probes to be used with simple instrumentation based on an LED light source, allowing low cost oxygen sensing in aqueous solutions. Other possible light sources include laser diodes, electroluminescent devices and flash lamps.

[Ru(dpp(SO$_3$Na)$_2$)$_3$]Cl$_2$.6H$_2$O has similar spectral properties and oxygen sensitivity to the unsulfonated metal-ligand complex, and thus is suitable as a water soluble oxygen sensor. [Ru(dpp(SO$_3$Na)$_2$)$_3$]Cl$_2$.6H$_2$O and the other water soluble oxygen sensors of the present invention are a mixture of several isomers: the location of the SO$_3$Na substituents on the phenyl rings are randomly positioned. However, there is no evidence for a heterogeneous mixture of long-lifetime probes as ascertained by frequency domain fluorometry. However, the spectral properties and decay times are not sensitive to the position of SO$_3$Na substitution, facilitating synthesis of the sensors. Use of a single isomer is not believed to be necessary.

Figure 3:
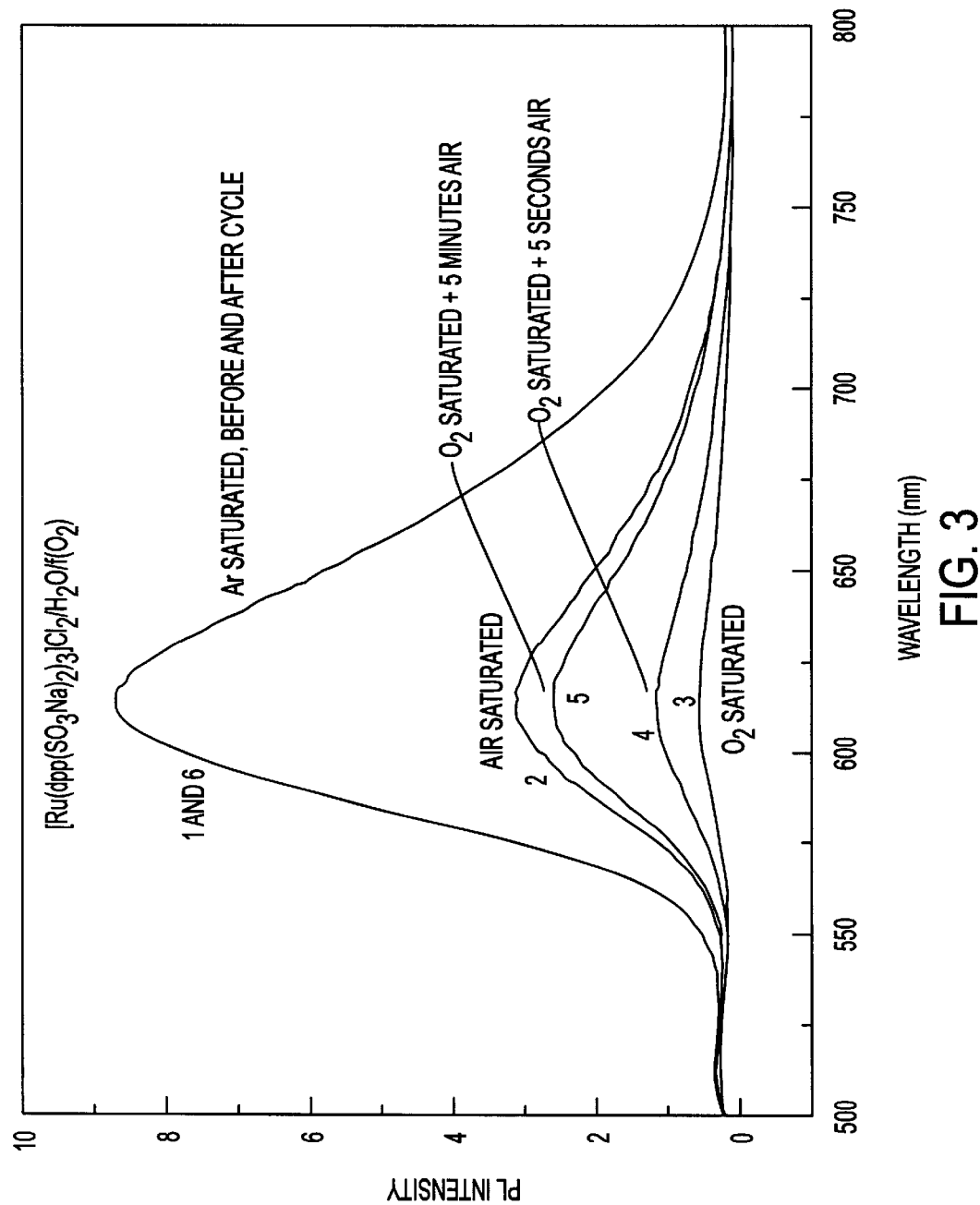
FIG. 3 graphically depicts the emission spectra of [Ru(dpp(SO$_3$Na)$_2$)$_3$]Cl$_2$ at equilibrium with argon, air, and 100% oxygen. Curve 3 is the spectrum of [Ru(dpp(SO$_3$Na)$_2$)$_3$]Cl$_2$ when O$_2$-saturated. Curves 4 and 5 are the spectrum of O$_2$-saturated [Ru(dpp(SO$_3$Na)$_2$)$_3$]Cl$_2$ exposed to air for 5 seconds and 5 minutes respectively. Curve 2 is the spectrum of [Ru(dpp(SO$_3$Na)$_2$)$_3$]Cl$_2$ when air-saturated. Curves 1 and 6 depict the spectrum of argon-saturated [Ru(dpp(SO$_3$ Na)$_2$)$_3$]Cl$_2$. The excitation wavelength in each case was 480 nm.
Figure 4:
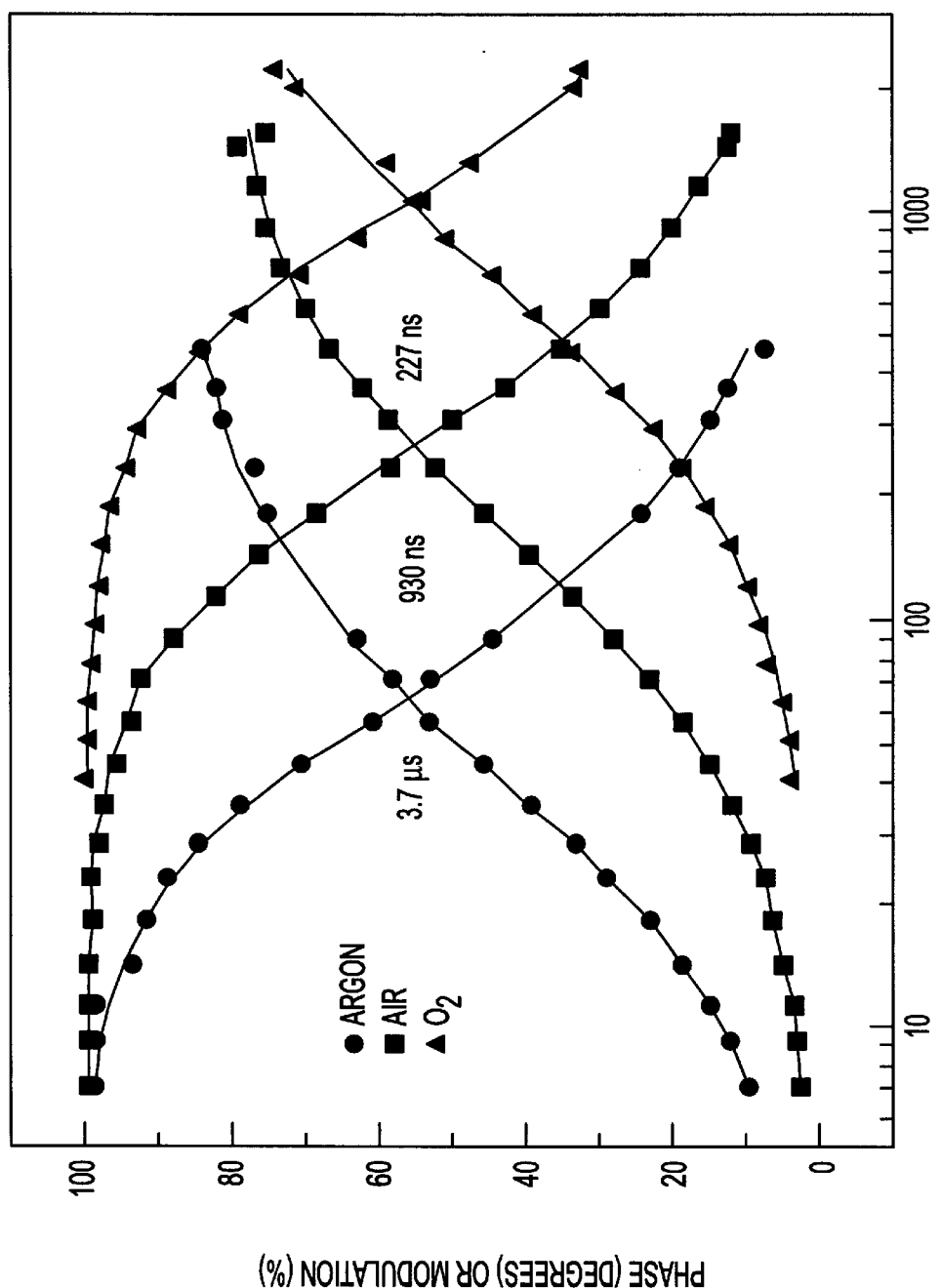
FIG. 4 graphically provides the frequency domain intensity decays of [Ru(dpp(SO$_3$Na)$_2$)$_3$]Cl$_2$ in equilibrium with argon, air, or 100% oxygen, representing different concentrations of oxygen. the excitation wavelength was 488 nm.
Figure 5:
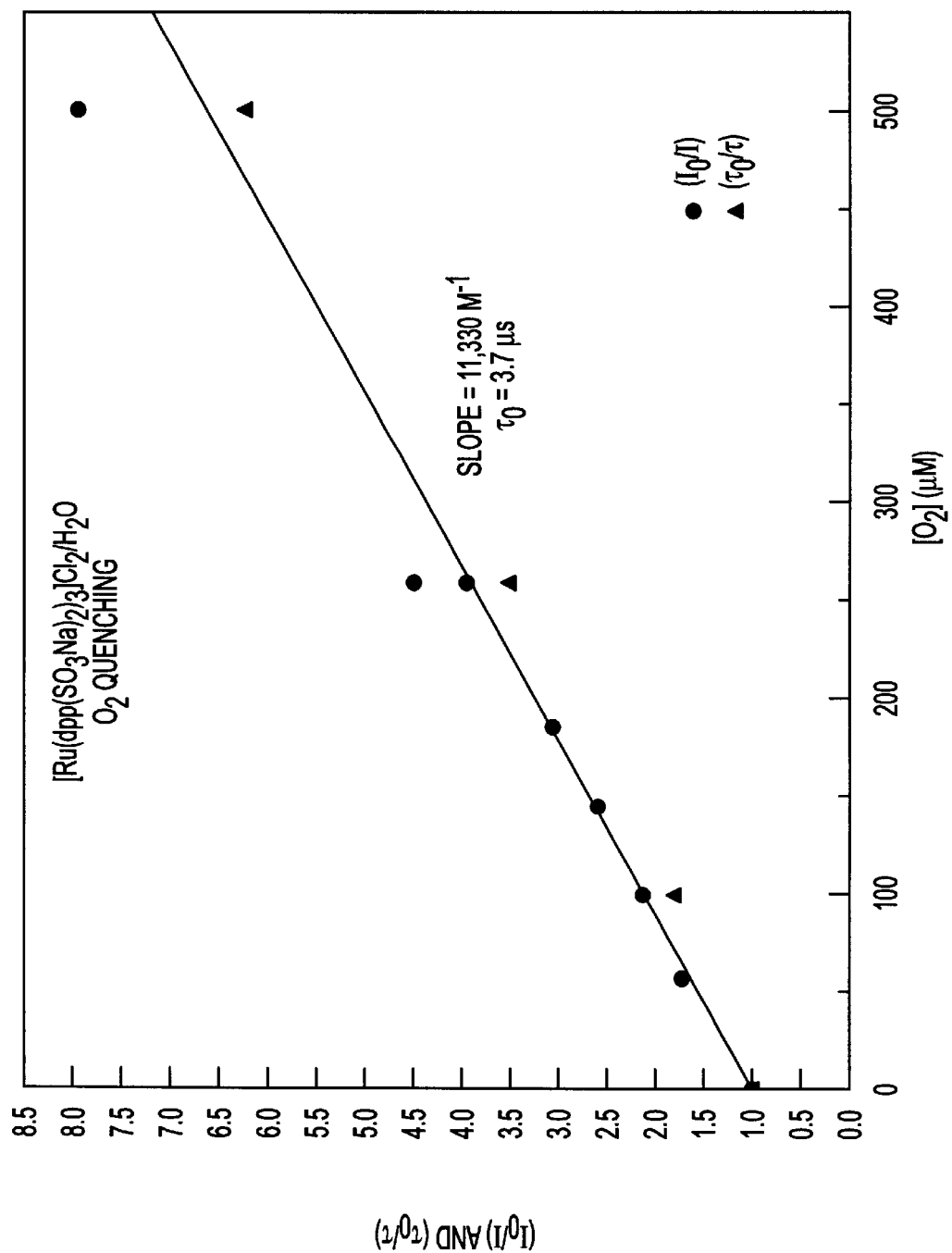
FIG. 5 is an oxygen Stern-Volmer plot graph for [Ru(dpp(SO$_3$Na)$_2$)$_3$]Cl$_2$ in water at 20° C. This plot depicts the O$_2$ quenching of the molecule.

The intensity of oxygen probe fluorescence decreases in the presence of oxygen and this quenching is reversed by removal of the oxygen (see FIG. 3). FIG. 4 shows the frequency domain lifetimes of [Ru(dpp(SO$_3$Na)$_2$)$_3$]Cl$_2$. The decrease in lifetime with increasing amounts of oxygen proves that the molecule is dynamically quenched, a property which allows oxygen concentration to be determined by measuring the decay time of the probe. These data are present as a Stern-Volmer plots. The Stern-Volmer plot for oxygen quenching is shown in FIG. 5, which is a representation of the change in fluorescence decay times with changing oxygen concentration. The Stern-Volmer equation for dynamic quenching of oxygen is $$I_0 = \tau_0 = 1 + k\tau_o[O_2] = 1 + K[O_2] \quad (1)$$

where $I_0$ and I are the fluorescence intensities in the absence and presence of oxygen, respectively, $\tau_0$ and $\tau$ are the decay times in the absence and presence of oxygen, respectively, $k_q$ is the bimolecular quenching constant, $K = k_q \tau_o$ is the Stern-Volmer quenching constant, and $[O_2]$ is the oxygen concentration. The slope of the Stern-Volmer plot is equal to K, and larger slopes indicate higher sensitivity to oxygen. The equivalent decrease in intensity and decay time ($I_0/I = \tau_0/\tau$) indicates the quenching is dynamic. A Stern-Volmer constant of 11,330 M$^{-1}$ indicates that the compound is highly sensitive to small amounts of dissolved oxygen and can be used to determine oxygen concentrations as low as 8.8 $\mu$M, which is equivalent to equilibration of water with 5.5 torr oxygen. With careful measurements of the intensity or lifetimes, still smaller oxygen concentrations could be measured with this water soluble oxygen probe. This Stern-Volmer quenching constant and unquenched lifetime (3.7 $\mu$s) correspond to a bimolecular quenching constant of 3.1×10$^9$ M$^{-1}$ sec$^{-1}$, which indicates that the quenching is diffusion controlled. The value of the bimolecular quenching constant indicates quenching is efficient, which provides the highest sensitivity to oxygen.

The long decay times of the sensors allow the emission to be detected following the decay of interfering prompt autofluorescence, which may occur in samples. Long decay time interferences are not frequently encountered, so that in most cases gated detection and decay time measurements may provide accurate measurements of the oxygen concentration under conditions encountered in day-to-day measurements. For example, suppose there is autofluoescence from the sample, which may be water from a boiler system, aquarium or cell culture medium. Most autofluorescence decays are on a nanosecond timescale. The emission from the water soluble oxygen sensor could be detected after the interfering signal has decayed.

In accordance with the present invention, there are many instances where water soluble sensors are of value. These sensors may be used to determine oxygen concentration in any aqueous environment for industrial and analytical applications. In one embodiment, aqueous samples are mixed with small amounts of a water soluble sensor and the oxygen concentration determined from the intensity or preferably the decay time of the sensor, which is insensitive to the probe concentration. Since the sensor concentration is not important and does not affect the decay time, measuring the exact amount or concentration of probe added is not necessary when determining oxygen concentration in this way. Thus, a concentrated solution of sensor may be added to the sample dropwise using an ordinary dropper bottle.

If fluorescence intensity is used to determine oxygen concentration, a known volume of sensor solution at a known concentration must be added to the sample. A wide range of concentrations of sensor are appropriate for use with the present invention using either method, for example about 10$^{-9}$ M to about 10$^{-3}$ M, or any concentration which yields a detectable fluorescence. Preferred concentrations of oxygen sensor are about 10$^{-4}$ M to about 10$^{-6}$ M. The oxygen concentration is calculated from the intensity or decay time of the sample, and use of the Stern-Volmer equation (equation 1, supra). In the case of intensity measurements, one measures the intensity in the absence of oxygen ($I_0$) and in the presence of the unknown amount of oxygen (I), allowing calculation of the oxygen concentration using a previously determined value of the Stern-Volmer constant (K). To avoid the need for measurement in the absence of oxygen, one can imagine an intensity calibration procedure which uses the intensity at atmospheric oxygen as the calibrating intensity.

The oxygen concentration can also be determined from the decay time. The decay time can be measured using either time-domain or phase-modulation methods. In a time-domain measurement the intensity is calculated from the slope of the intensity decay, following excitation with a pulse of light shorter than the decay time. The time-dependent decay is given by $$I(t) - I(0)\exp(-t/\tau) \quad (2)$$

where t is time, $\tau$ is decay time and I(0) is the intensity at t=0. The decay time can also be determined from the phase angle ($\phi$) or modulation (m) of the emission, relative to the intensity-modulated excitation. In this case the decay time is calculated using $$\tan \phi = \omega \tau \quad (3)$$

$$m = (1 + \omega^2 \tau_2)^{1/2} \quad (4)$$

where $\omega$ is the excitation light modulation frequency in radians/sec.

The use of decay times is advantageous because only a single measurement is needed. Assuming the signal is adequate, decay times are independent of the total intensity of signal. One can make a calibration curve of T,ø, or m versus oxygen concentrations, and calculate the oxygen concentration from a single measurement of T, ø or m.

The preferred compound is chemically stable and can be readily mixed with water. Accordingly, test kits containing dropper bottles with highly concentrated solutions of a water soluble oxygen sensor such as $[Ru(dpp(SO_3Na)_2)_3]^{2+}$ or any of the compounds shown in FIG. 8 are contemplated by the present invention. Kits could also contain sealed ampules of known sensor concentration and volume, for addition of precise amounts of sensor to a known volume of sample. Other possible embodiments for kits are readily understood by those of skill in the art. The concentrated solution can be added to freshly drawn water samples, or any other aqueous sample for which the oxygen concentration is desired to be known. The oxygen concentration could then be determined from the intensity or preferably from the decay time of the oxygen sensor.

Another potential application of water soluble oxygen sensor compounds is oxygen imaging in tissues or in cells. In the case of fluorescence microscopy, the water soluble oxygen sensor could be added to cells by microinjection and the oxygen concentration determined from the decay times or fluorescence lifetime imaging microscopy (FLIM). Alternatively, the water soluble probe may be made cell-permanent. The addition of lipophilic side chains which are cleaved by intracellular enzymes, allows the probe to be taken up by cells and then trapped within the cells when the lipophilic side chains are removed. ($[Ru(bpy)_3]Cl_2$) has been used for oxygen imaging in cells (Gerritsen, H. C. et al., *J. Fluoresc.*, 7:11–15 (1997)), even though its lifetime is 10-fold less than $[Ru(dpp(SO_3Na)_2)_3]^{2+}$ and it is thus much less sensitive to oxygen. The inventive water soluble probes, particularly the preferred probe, $[Ru(dpp(SO_3Na_2)_3]Cl_2$, can be expected to be considerably more sensitive than $[Ru(bpp)_3]Cl_2$.

Another application of a water soluble oxygen sensor is imaging of intracellular oxygen concentrations. To facilitate such applications, water soluble oxygen sensors such as the preferred ruthenium complex shown in FIG. 1 were developed. In this embodiment, a water soluble oxygen sensor is used to label cells which are examined by fluorescence microscopy. The oxygen concentration image can be calculated from the decay times measured at each position in the sample. Methods for decay time imaging are well know in the art, and include the use of gated image intensifiers to measure images at various time intervals following pulsed excitation. Decay time images can also be measured using a gain-modulated image intensifier to determine the phase angle and modulation of the emission at each point in the image. Oxygen concentration images can also be obtained from intensity images, but this requires collection of a calibration image in the absence of oxygen.

EXAMPLES

1. Synthesis of $[Ru(dpp(SO_3Na)_2)_3]Cl_2 \cdot 6H_2O$ $[Ru(dpp(SO_3Na)_2)_3]Cl_2 \cdot 6H_2O$ was synthesized according to the following method. $RuCl_3$ (57 mg, 0.0276 mmol, Aldrich) was reacted with 3.5 equivalents of 4,7-diphenyl-1,10-phenanthrolinedisulfonic acid disodium salt (518 mg, 0.0965 mmol, Aldrich) in 20 ml deionized $H_2O$ and refluxed with stirring for 2 days. The solution changed from dark green to red over this time. The solution was then cooled to room temperature and filtered. The solvent was removed by rotary evaporation and the resulting solid redissolved in 5 ml $H_2O$. This solution was loaded onto a Sephadex LH-20 column (25×2 cm, Pharmacia) and eluted with $H_2O$. The first brown and purple bands were discarded and the red fraction collected. The red fraction was evaporated to dryness to give a red solid. Characterization was consistent with results reported by Anderson et al.

2. Determination of Quenching Constants of Water-Soluble Oxygen Sensors

Oxygen Stern-Volmer quenching constants ($K_{SV}$) and bimolecular quenching constants were determined by varying the $O_2$ concentration in aqueous solutions containing $[Ru(dpp(SO_3Na)_2)_3]Cl_2$. Oxygen (>99%) was mixed with argon by using a Linde mass flow controller to yield gases of a defined percent $O_2$ composition. The gas mixture was pre-bubbled through 100 ml $H_2O$, and then bubbled through the analyte solution. The precision of the gas mixing device is specified to be within ±1%. The concentration Of $O_2$ in $H_2O$ was determined by scaling the %$O_2$ in the gas to that of the total solubility of $O_2$ in $H_2O$ (0.00125 M at 100% $O_2$).

The dynamic nature of oxygen quenching $[Ru(dpp(SO_3Na_2)_3]Cl_2$ is shown by the frequency-domain intensity decays (FIG. 4). According to well known theory for quenching, an equivalent decrease in intensity and lifetime ($I_0/I=T_0/T$) proves that the quenching is due to diffusive encounters of the probe with the oxygen. Static quenching is due to ground state complex formation of the probe and quenchers, and does not cause a decrease in decay time. The dynamic quenching process is believed to be due to energy transfer to form singlet $O_2$, but other mechanisms are possible. In the absence of oxygen, the decay is nearly a single exponential with a decay time of 3.7 μs. However, a small component with a fractional intensity near 1% and a lifetime of 0.17 μs was observed (Table I). This short component appears to be unaffected by $O_2$ in all measurements, which leads us to believe that it may be a result of using the frequency domain method. In fact, previous time domain work shows homogeneous decays with related Ru(II) compounds (Anderson, S. et al., *J. Chem. Soc. Dalton Trans.*, 2247–2261 (1985)).

TABLE I

Intensity decay analysis of
$[Ru(dpp(SO_3Na_2)_3]Cl_2$ quenched by dioxygen in
various biological media.[a]

| Sample | $\tau_i$ (μs) | $\alpha_i$ | $f_i$ | <τ> (μs)[d] | $X_R^2$ |
|---|---|---|---|---|---|
| $H_2O$, Ar | 3.64 | 0.82 | 0.99 | | 0.213 (21.3)[3] |
| | 0.166 | 0.18 | 0.01 | 3.61 | |
| $H_2O$, Air | 0.953 | 0.78 | 0.98 | | |
| | 0.075 | 0.22 | 0.02 | 0.933 | 1.55 (37.5) |
| $H_2O$, 100% $O_2$ | 0.227 | 1.0 | 1.0 | 0.227 | 3.3 (3.3) |
| HSA,[b] Argon | 5.44 | 0.40 | 0.68 | | |
| | 2.29 | 0.41 | 0.30 | | |
| | 0.235 | 0.19 | 0.02 | 4.41 | 0.694 (105) |
| HSA,[b] Air | 3.69 | 0.41 | 0.78 | | |
| | 0.733 | 0.59 | 0.22 | 3.03 | 2.88 (105) |
| | 4.1 | 0.3 | 0.68 | | |
| | 1.12 | 0.49 | 0.29 | | |
| | 0.238 | 0.2 | 0.03 | 3.12 | 0.566 (244) |
| DPPG,[c] Argon | 3.78 | 0.79 | 0.99 | | |
| | 0.171 | 0.21 | 0.01 | 3.73 | 0.235 (19.8) |
| DPPG,[c] Air | 0.734 | 0.78 | 0.95 | | |
| | 0.148 | 0.22 | 0.05 | 0.702 | 3.01 (23.7) |

[a]Frequency-domain intensity decays obtained with 488 nm excitation and a 610 nm long pass filter.
[b]HSA (5 mg/ml), phosphate buffer, pH 7.2.
[c]DPPG lipid vesicles (2 mg/ml), TRIS, 50 mM KCL, pH 7.5.
[d]Calculated from <τ> = Σ$f_i \tau_i$.
[e]The values in parentheses are the $X_R^2$ values for the single decay time fit.

The decay times and the intensities in the presence of various amounts of dissolved oxygen were used to determine the oxygen Stern-Volmer quenching constant (FIG. 5).

Essentially the same results were obtained from the decrease in intensity and lifetime. More explicitly, the intensity and decay times decreased by a similar proportional amount in response to oxygen. The small differences between the various measurements are thought to result from less than complete equilibration with various concentrations of dissolved oxygen.

3. Determination of Absorption Spectra of [Ru(dpp(SO$_2$Na)$_2$)$_3$]

Electronic absorption spectra were measured on a Hewlett Packard HP-8453 spectrophotometer. Steady-state photoluminescence spectra were acquired on a SLM Aminco AB-2 spectrofluorimeter with 480±2 nm excitation. The optical density of [Ru(dpp(SO$_3$Na)$_2$)$_3$]Cl$_2$ was at or below 0.2 at 480 nm during all measurements. Time-resolved photoluminescence decays were measured in the frequency-domain with instrumentation that has been described by Lakowicz and Gryczynski (Topics in Fluorescence Spectroscopy, vol. 1: Techniques, (J. R. Lakowicz, Ed.) Plenum Press (1991), New York, pp. 293–355). The excitation source was an air-cooled CW Ar$^+$ laser (543-AP, Omnichrome) tuned to the 488.0 nm line. The laser was amplitude modulated with a low frequency modulator (K2.LF, ISS) and input into an ISS frequency-domain fluorimeter (Koala). Data was collected at approximately 20 distinct frequencies between 7 kHz and 2 MHZ. Emission was collected through a 610 nm cutoff filter (Corning 2-61) and Texas Red with a lifetime of 4 ns was used as a lifetime reference.

Figure 2:
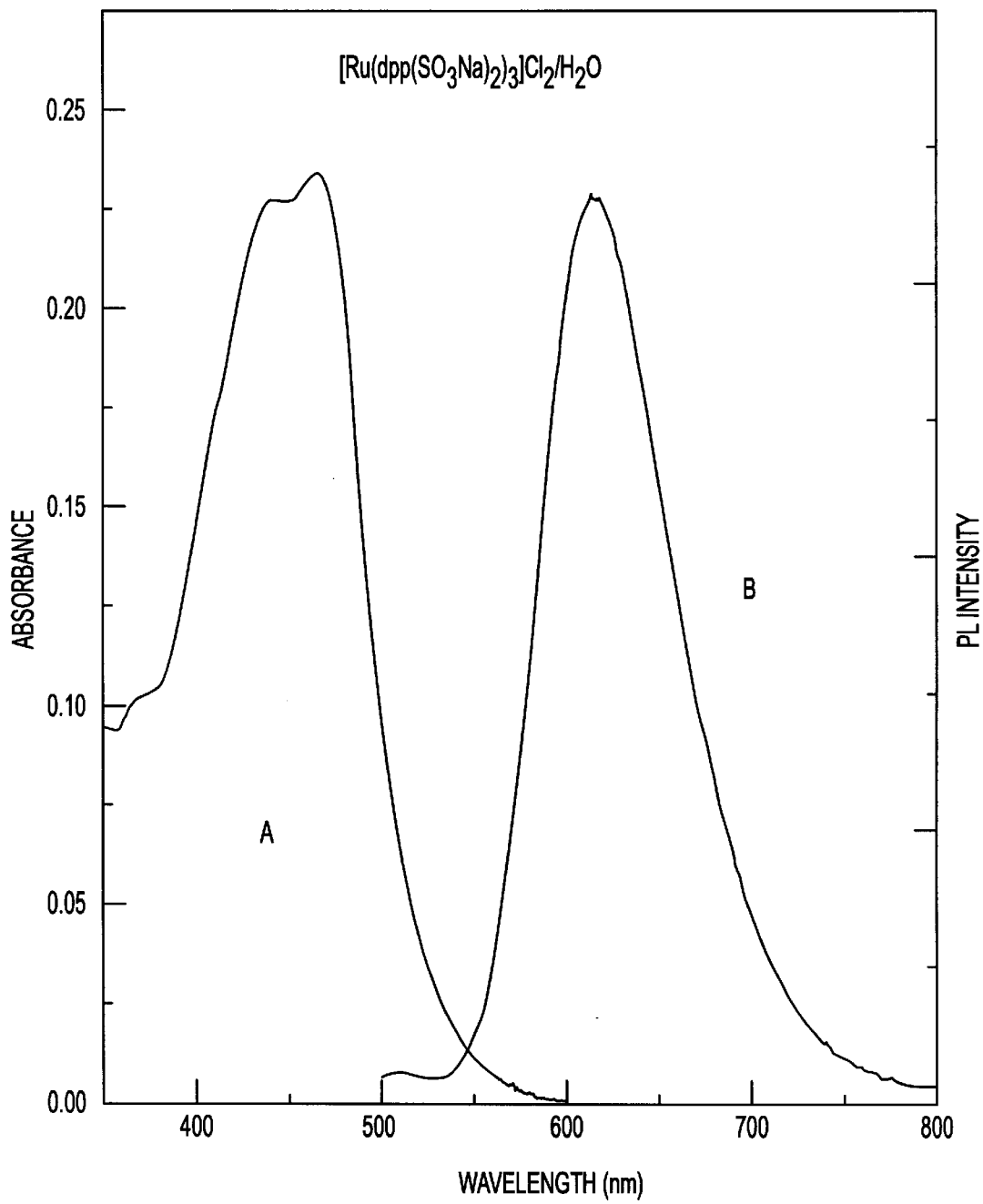
FIG. 2 graphically gives the absorption and emission spectra of [Ru(dpp(SO$_3$Na)$_2$)$_3$]Cl$_2$ in water. The excitation wavelength was 480 nm. Curve A represents the absorption spectrum while curve B represents the emmission spectrum.

Absorption and emission spectra of [Ru(dpp(SO$_3$Na)$_2$)$_3$]$^{2+}$ when dissolved in water are shown in FIG. 2. The spectra are similar to that displayed by [Ru(dpp)$_3$]$^{2+}$. The absorption near 480 nm allows excitation with blue light emitting diodes (LEDs). The large Stokes' shift is a favorable property of this class of compounds because it allows for easy rejection of scattered light. Additionally, a large Stokes' shift typically means that the lumiphores will not self-quench by probe-probe interactions.

Emission spectra of [Ru(dpp(SO$_3$Na)$_2$)$_3$]$^{2+}$ are shown in FIG. 3. In the presence of dissolved oxygen from the air, the intensity decreases 2.9-fold, compared to that in the absence of oxygen. In the presence of dissolved oxygen equivalent to 100% O$_2$, the intensity decreases 16.4-fold, relative to the O$_2$-free solution. The quenching by oxygen is easily reversible by removal of dissolved oxygen and completely reversible when all of the oxygen is removed by purging with argon.

4. Use of the Invention in a Biological Environment

Figure 6:
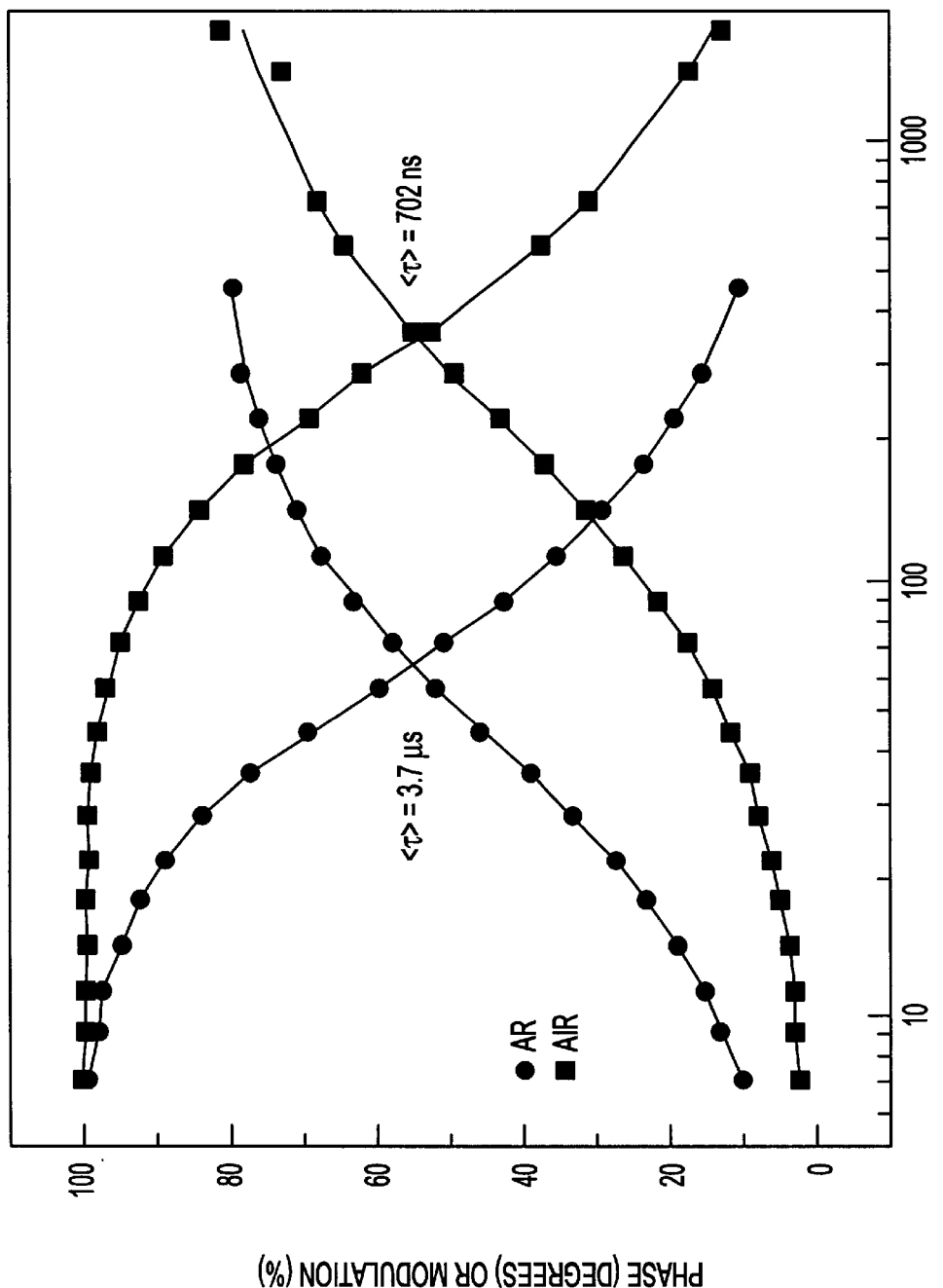
FIG. 6 graphically furnishes the frequency domain intensity decays of [Ru(dpp(SO$_3$Na)$_2$)$_3$]Cl$_2$ in the presence of DPPG vesicles (2 mg/ml) at equilibrium with argon and air.
Figure 7:
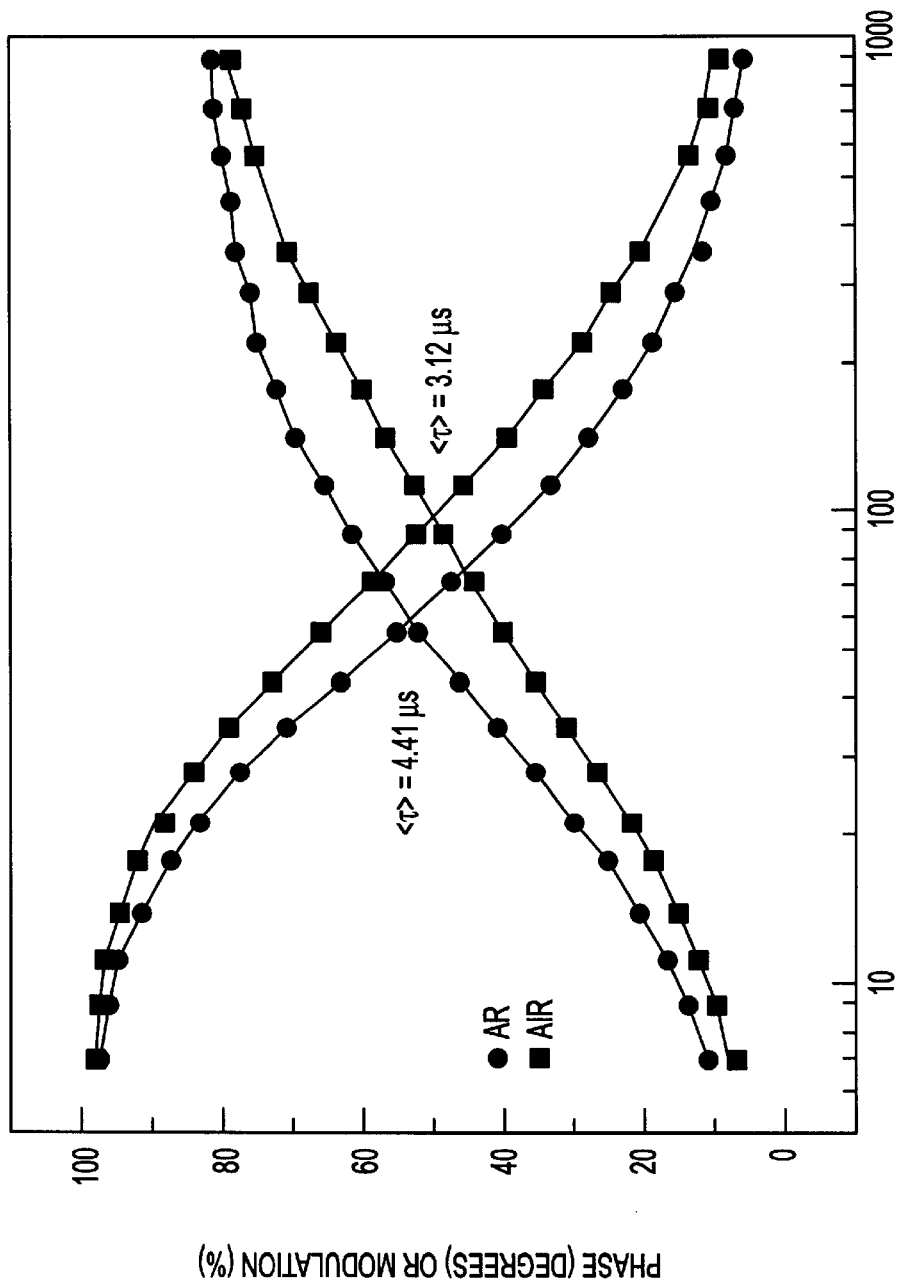
FIG. 7 graphically gives the frequency domain intensity decays of [Ru(dpp(SO$_3$Na)$_2$)$_3$]Cl$_2$ in the presence of HSA (5 mg/ml) in phosphate buffer, pH 7.2, at equilibrium with argon and air.
Figure 8A:
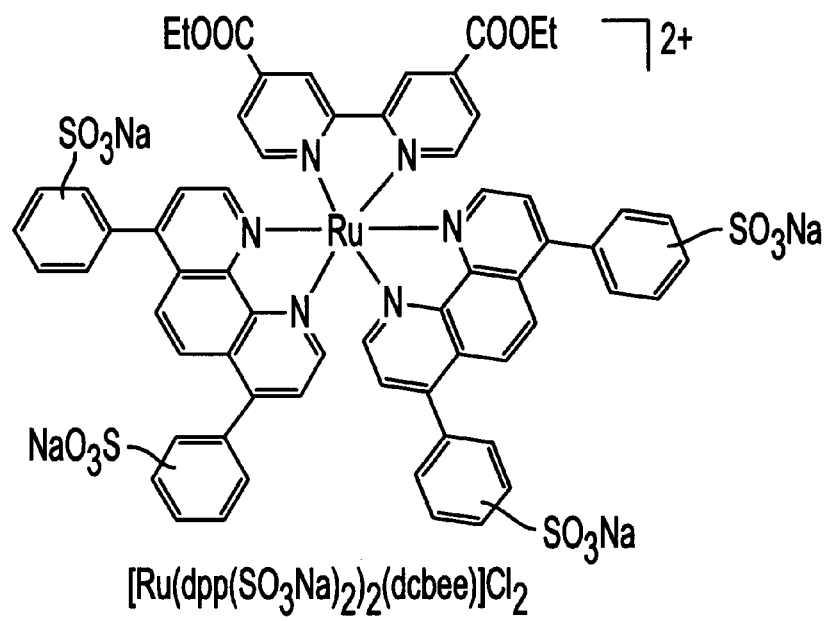
FIG. 8 provides the chemical structures of inventive water soluble oxygen sensors based on transition metal complexes.
Figure 8B:
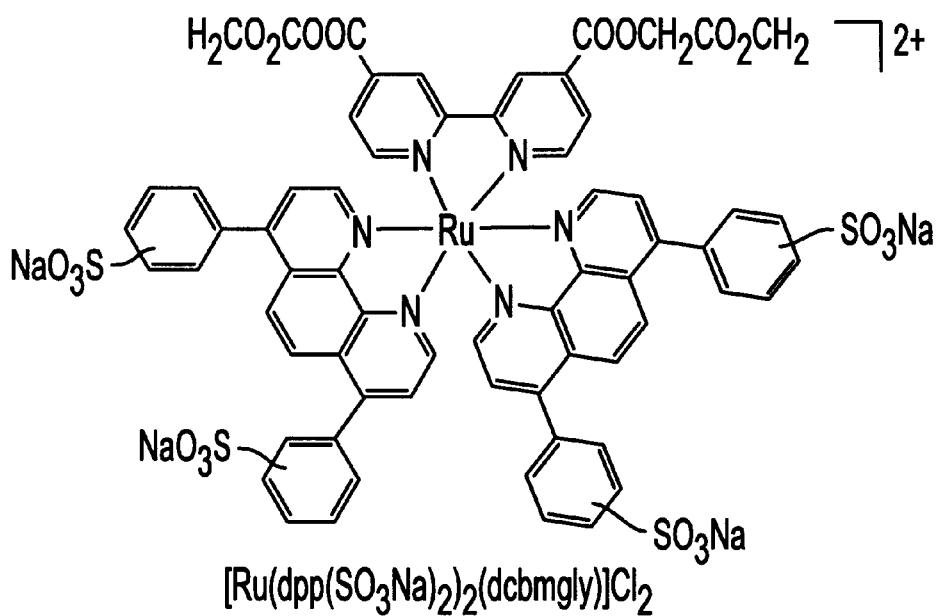
Figure 8C:
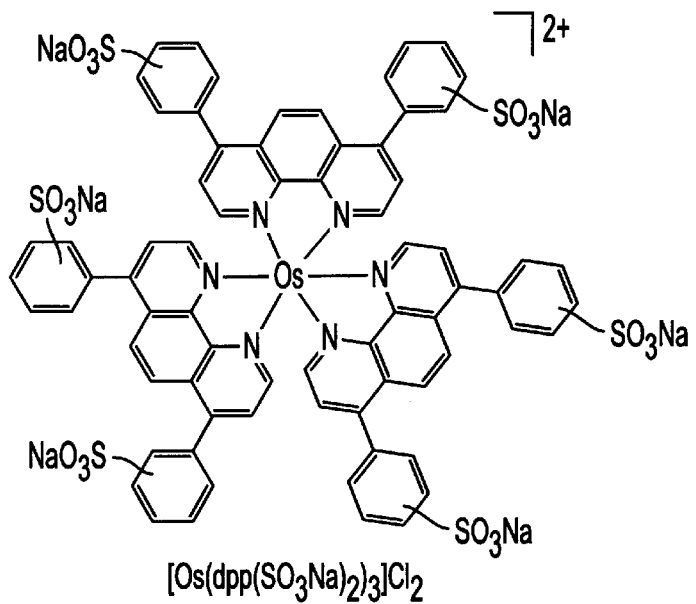
Figure 8D:
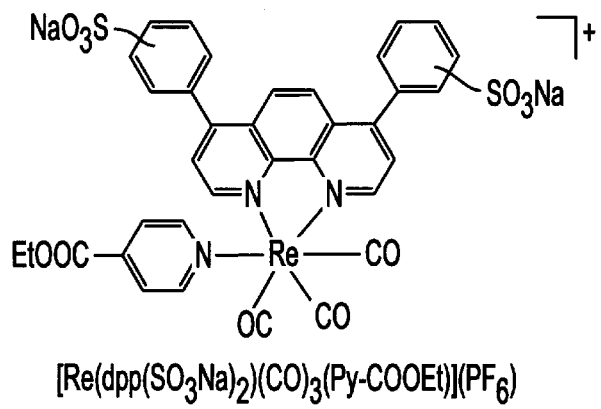
Figure 8E:
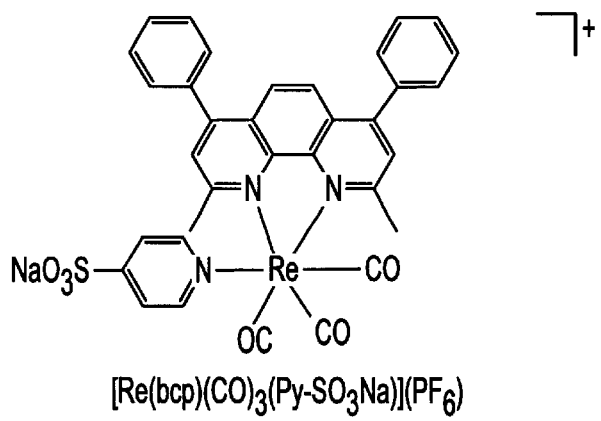
Figure 9A:
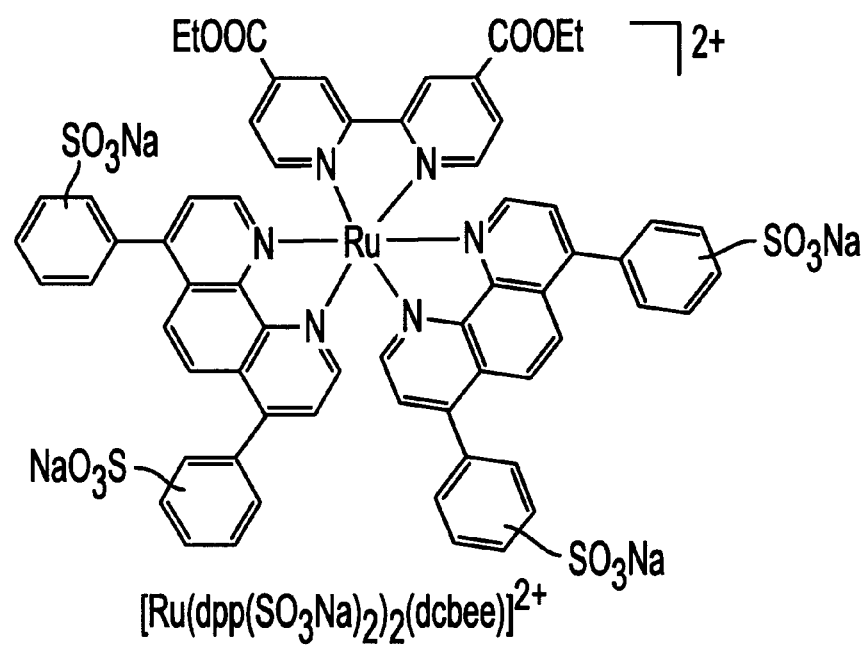
FIGS. 9a–9e provide the chemical structure of additional water soluble oxygen sensors based on transition metal complexes.
Figure 9B:
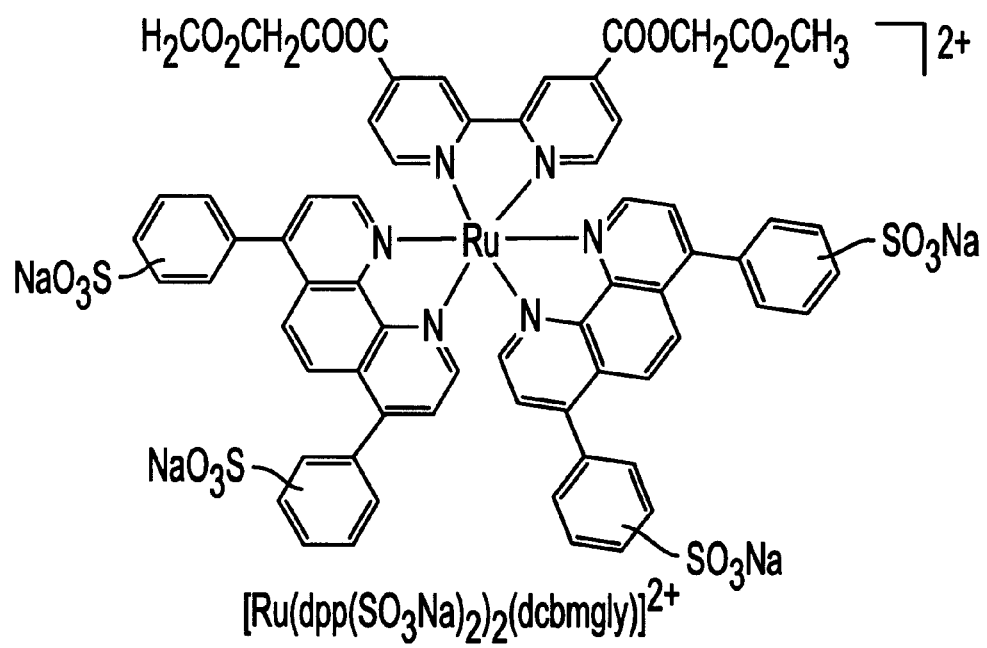
Figure 9C:
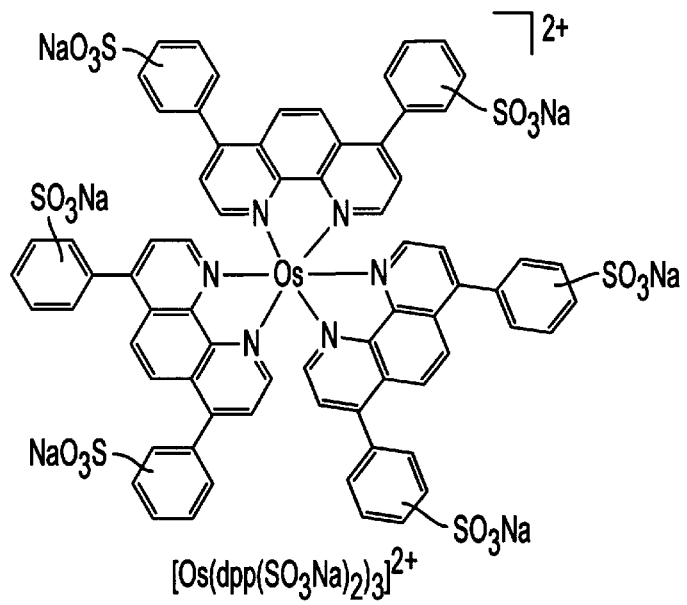
Figure 9D:
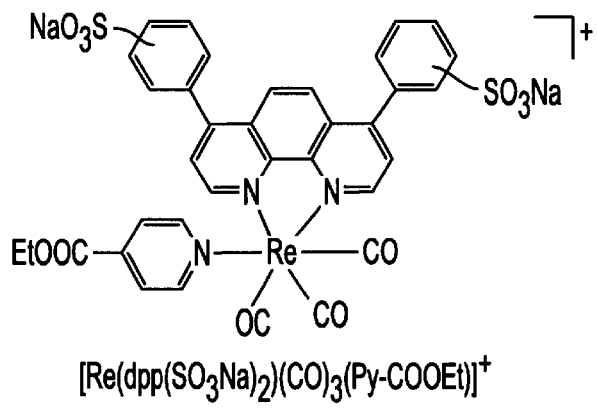
Figure 9E:
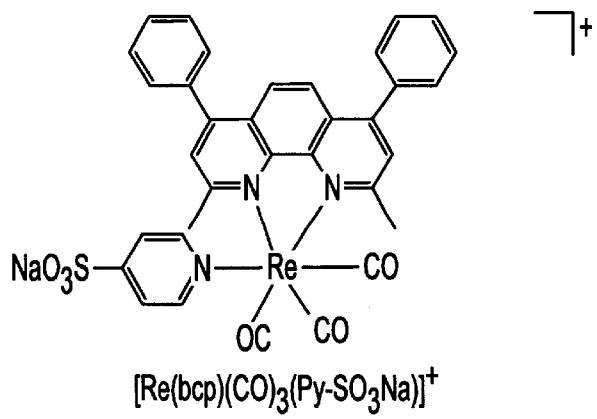
Figure 10A:
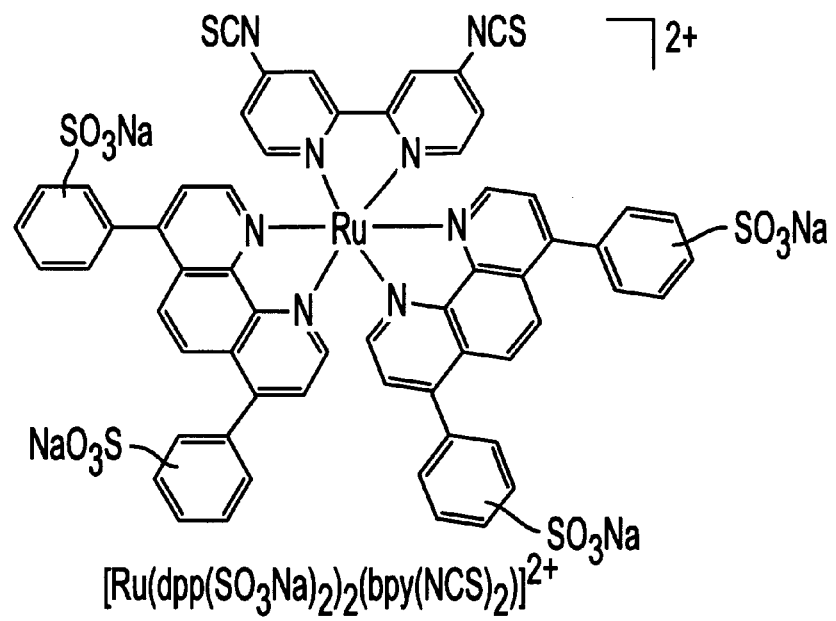
FIGS. 10a–10f provide the chemical structure of water soluble sensors which can be linked to lipids, proteins or saccharides.
Figure 10B:
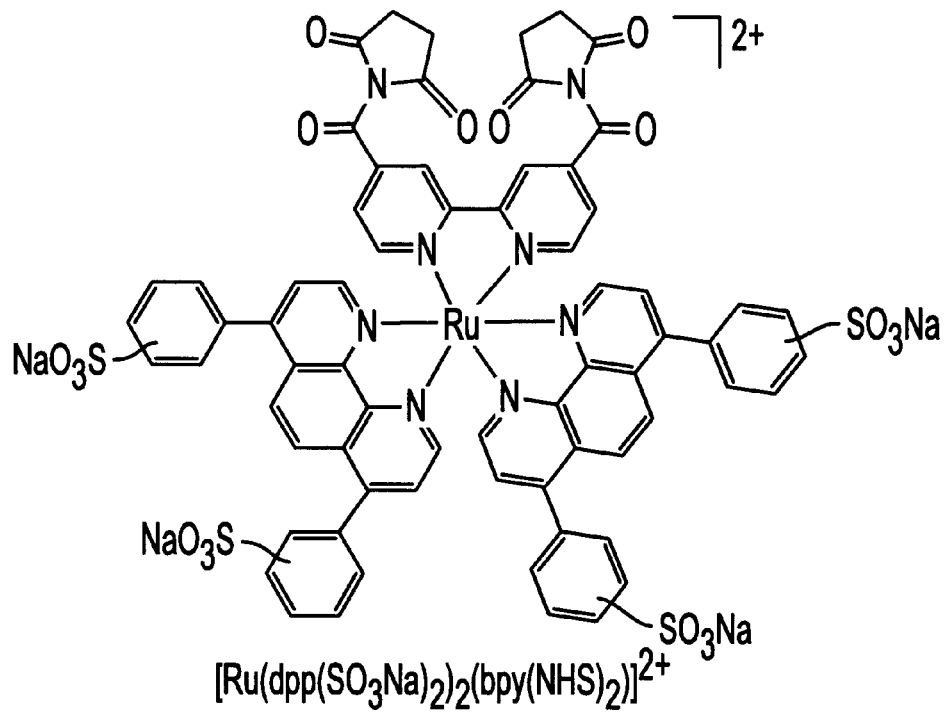
Figure 10C:
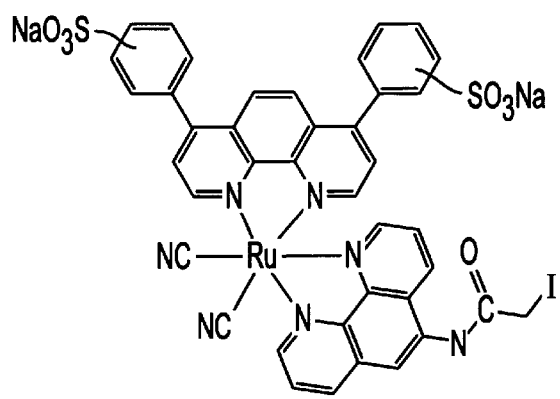
Figure 10D:
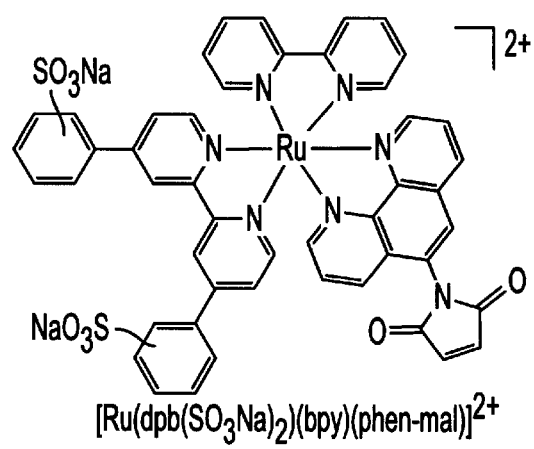
Figure 10E:
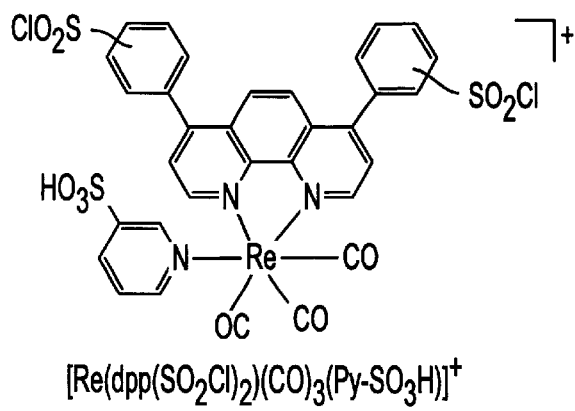
Figure 10F:
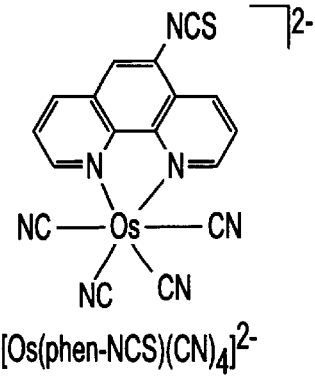
Figure 11A:
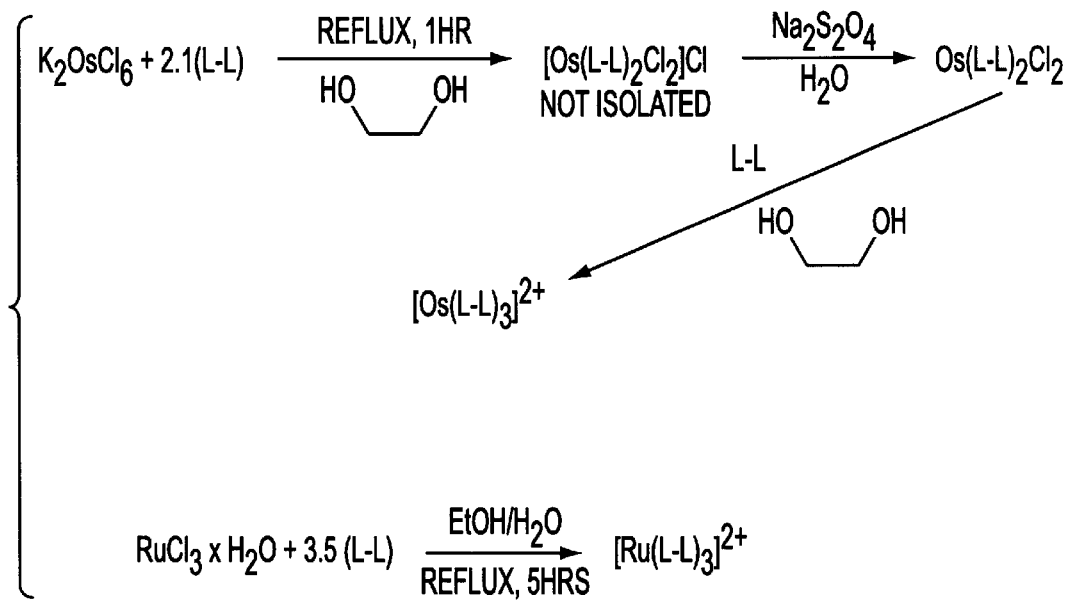
FIGS. 11a–11d show routes of chemical synthesis of compounds in accordance with the invention.
Figure 11B:
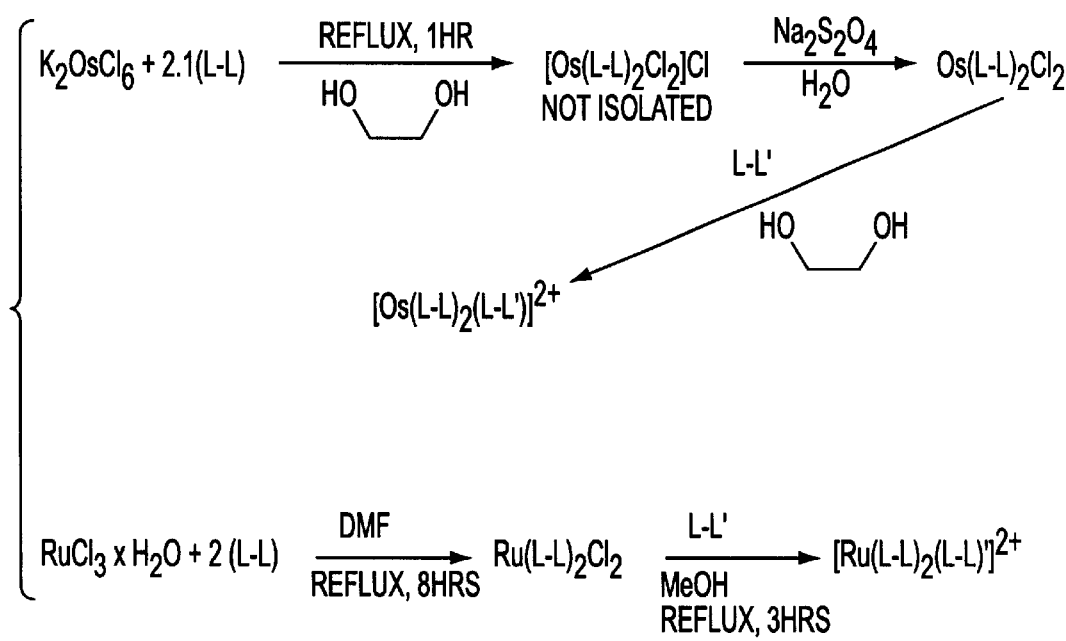
Figure 11C:
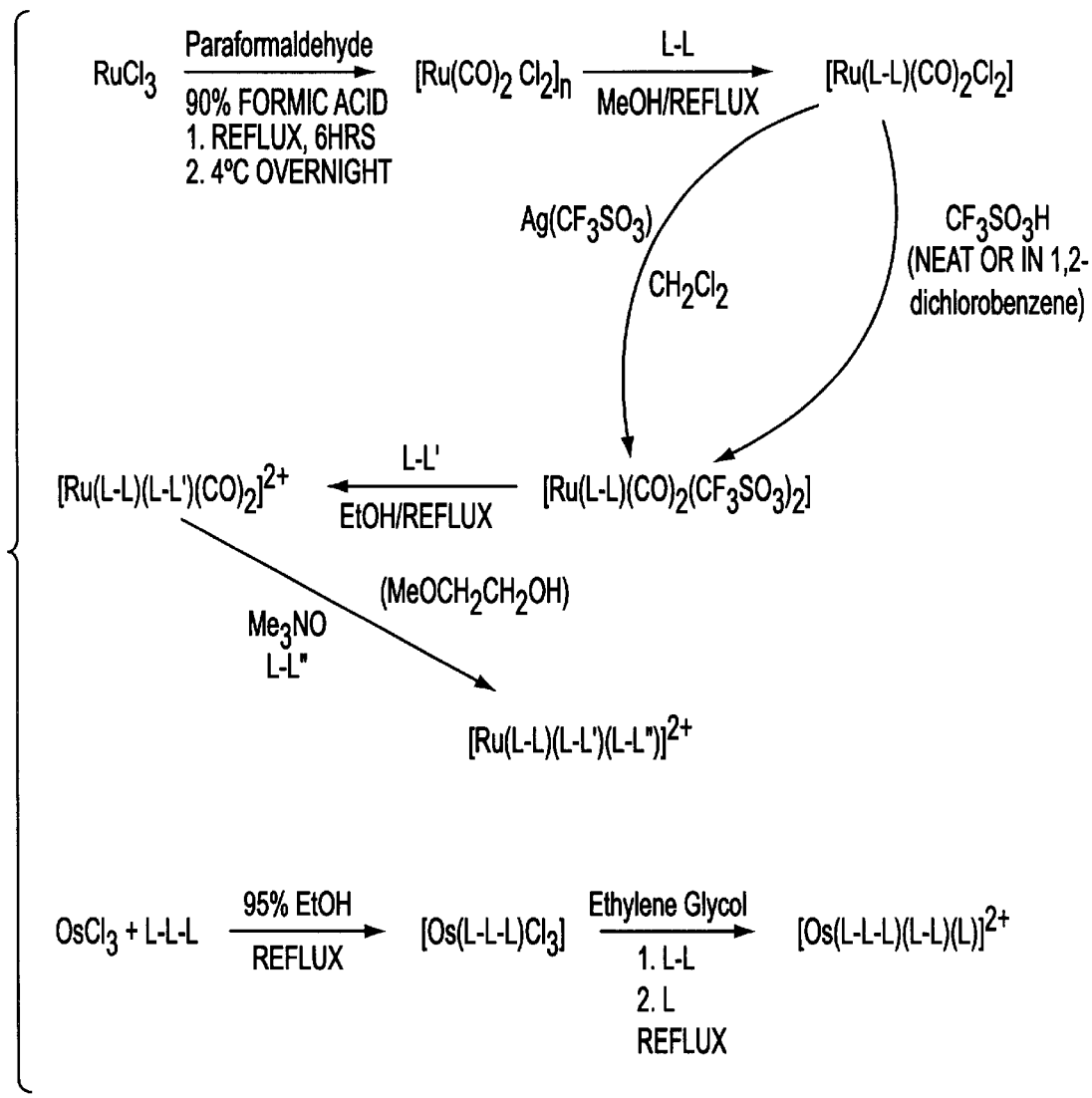
Figure 11D:
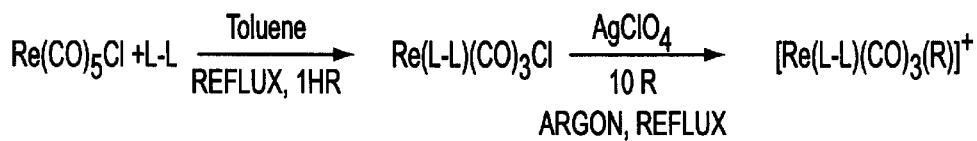

If the sensor is to be used with biological compounds, it is important to understand whether its intensity, intensity decay or sensitivity to oxygen will be altered by the presence of large quantities of biological substances. Hence, the intensity decay of [Ru(dpp(SO$_3$Na$_2$)$_3$]Cl$_2$ was examined in the presence of dipalmitoyl-L-2-phosphatidylglycerol (DPPG, Sigma) vesicles (FIG. 6) and in the presence of human serum albumin (HSA, Sigma) (FIG. 7). Lipid vesicles were prepared by sonication of 2 mg/ml DPPG in 10 mM TRIS with 50 mM, KCl at pH 7.5. Experiments with HSA were conducted in 0.1M sodium PO$_4$ buffer, pH 7.2. The lipid vesicles appear to have minimal effect on the intensity decay of [Ru(dpp(SO$_3$Na$_2$)$_3$]Cl$_2$. In the absence of oxygen, the intensity decay was essentially the same in the presence or absence of the DPPG vesicles (Table I). However, the probe does display interactions with human serum albumin (FIG. 7). In the absence of oxygen, the mean decay time increases to 4.1 µs and the decay becomes more heterogeneous. This can be seen by the multi-exponential fits in Table I, and by the increase in the $\chi_R^2$ values for the single decay time fits. In the presence of HSA, the probe also becomes less sensitive to quenching by oxygen: the presence of dissolved oxygen from the air results in decreases in lifetime to 3.1 µs with HSA compared to 930 ns in its absence. Hence, the extent of oxygen quenching is clearly sensitive to binding to HSA. HSA is an unusual protein with high affinity for hydrophobic anions, and it is not clear that the oxygen sensor will display changes in oxygen sensitivity in the presence of less hydrophobic proteins. The effects of interactions with macromolecules or biomolecules can be accounted for in several ways. The calibration curves can be determined in the type of sample in which the actual measurements will be performed. In this instance, one can use probes which interact with the macromolecules. Alternatively, the actual charge and/or structure of the molecule may be changed to minimize its interactions with macromolecules. As an example, a positively charged probe (FIG. 9) may show lower affinity for albumins. Finally, one may covalently couple the probe to the macromolecule, such as a probe linked to lipid molecules or to proteins (FIG. 10). In this case the probe molecule interactions may remain the same irrespective of other macromolecules in the sample.

5. Data Analysis

The frequency domain intensity decay data were fit to single and multi-exponential models. The analysis of these decays were performed with non-linear least squares procedures described by Lakowicz and Grycaynski. The intensity decays were described by equation 1:

$$I(t) = \sum_i \alpha_i e^{-t/\tau_i} \qquad (1)$$

where $\alpha_i$ are the amplitudes of each component of the decay and $\tau_i$ are the respective decay times, and $\Sigma \alpha_i = 1.0$.

With a water soluble oxygen sensor, a number of applications can be realized. An oxygen sample can be obtained from the site of interest, which can be an ocean or lake sample, from process water in an industrial site, or in a heating/cooling system. A drop of sensor solution is added to the sample. A small instrument excites the sample using a LED or other simple light source. The emission is detected with a photomultiplier tube or solid state detector. The intensity, decay time, phase angle or modulation then is used to calculate the oxygen concentration.

This method is usable for measurement in biological samples, such as in blood or through skin. Longer wavelength sensors such as those containing osmium can be used to avoid tissue absorption. The probe can then be excited with light above 600 nm, which is weakly absorbed by tissues. The emitted light can be detected, allowing calculation of oxygen concentrations below skin, in blood samples, or even in intact human brains.

What is claimed is:

1. A method of conducting an assay of a sample containing oxygen in aqueous solution, comprising the steps of:

a) bringing a solution containing a water-soluble metal ligand complex into direct contact with said sample containing oxygen in aqueous solution so as to form a mixture;

b) irradiating said mixture with electromagnetic light energy so as to cause emission of light indicative of said oxygen in said sample; and c) measuring the emitted light and utilizing the measurements of the emitted light so as to determine oxygen concentration of said sample, wherein said metal ligand complex is selected from the group consisting of [Ru(dpp($SO_3$Na)$_2$)$_3$]$Cl_2$, [Ru(dpp($SO_3$Na)$_2$)$_2$(dcbee)]$Cl_2$, [Ru(dpp($SO_3$Na)$_2$)$_2$(dcbmgly)]$Cl_2$, [Os(dpp($SO_3$Na)$_2$)$_3$]$Cl_2$, [Re(dpp($SO_3$Na)$_2$)(CO)$_2$, (Py-COOEt)]($PF_6$), and [Re(bcp)(CO)$_2$ (Py-$SO_3$Na)]($PF_6$).

2. The method of claim 1 wherein the intensity of said emitted light is measured so as to determine the oxygen concentration of said sample.

3. The method of claim 1 wherein the lifetime of said emitted light is measured, so as to determine the oxygen concentration of said sample.

4. The method of claim 1 wherein said water soluble metal ligand complex is [Ru(dpp($SO_3$Na)$_2$)$_2$]$Cl_2$.

5. The method of claim 1, wherein the concentration of the water soluble metal ligand complex in the mixture is from about $10^{-9}$ M to about $10^{-3}$ molar.

6. The method of claim 5, wherein the concentration of the water soluble metal ligand complex in the mixture is from about $10^{-6}$ M to about $10^{-4}$ molar.

7. The method of claim 1, wherein the decay time of said emitted light is measured, so as to determine the oxygen concentration of said sample.

8. The method of claim 7, wherein the decay time is measured using a time-domain method.

9. The method of claim 7, wherein the decay time is measured using a phase-modulation method.

* * * * *